(12) United States Patent
Seligman et al.

(10) Patent No.: US 6,425,166 B1
(45) Date of Patent: Jul. 30, 2002

(54) STRAP TAB CAP FOR A KNEE BRACE

(75) Inventors: Scott Seligman; Brent R. Wiltshire, both of Carlsbad, CA (US)

(73) Assignee: DJ Orthopedics, LLC, Vista, CA (US)

( * ) Notice: Subject to any disclaimer, the term of this patent is extended or adjusted under 35 U.S.C. 154(b) by 0 days.

(21) Appl. No.: 09/945,120

(22) Filed: Aug. 31, 2001

(51) Int. Cl.[7] .............................................. A44B 1/00
(52) U.S. Cl. .......................................... 24/265; 602/26
(58) Field of Search ........................... 602/16, 5, 6, 12, 602/19, 20, 21, 23, 26, 27, 28, 29; 24/324, 662, 3.13, 265 AL, 265 BC, 265 A; 403/374.2, 374.1, 373

(56) References Cited

U.S. PATENT DOCUMENTS

| | | | | |
|---|---|---|---|---|
| 49,305 A | * | 8/1865 | Ruggles | 24/108 |
| 243,605 A | * | 6/1881 | Ott | 24/265 A |
| 932,177 A | | 8/1909 | Roth | |
| 1,927,061 A | * | 9/1933 | Chapman | 24/1 |
| 2,090,367 A | * | 8/1937 | Janes | 24/324 |
| 2,615,218 A | * | 10/1952 | Ross | 24/194 |
| 2,636,234 A | * | 4/1953 | Reiter | 24/324 |
| 3,528,412 A | | 9/1970 | McDavid | |
| 4,773,404 A | * | 9/1988 | Townsend | 602/16 |
| 4,955,369 A | | 9/1990 | Bledsoe et al. | |
| 5,086,760 A | * | 2/1992 | Neumann et al. | 602/16 |
| 5,288,287 A | | 2/1994 | Castillo et al. | |
| 5,292,303 A | | 3/1994 | Bastyr et al. | |
| 5,383,845 A | | 1/1995 | Nebolon | |
| 5,409,449 A | | 4/1995 | Nebolon | |
| 5,458,565 A | | 10/1995 | Tillinghast, III et al. | |
| 5,624,390 A | * | 4/1997 | Van Dyne | 482/124 |

* cited by examiner

Primary Examiner—Angela D. Sykes
Assistant Examiner—Fenn Mathew
(74) Attorney, Agent, or Firm—Knobbe, Martens, Olson & Bear, LLP

(57) ABSTRACT

The present invention provides a strap tab cap for connecting a strap tab to a knee brace wherein the strap tab cap has a very low profile and can rotate within a limited range. The low profile of the strap tab cap reduces the possibility that the knee brace will catch on a foreign object during physical activity. The rotation of the strap tab cap allows the strap to conform more easily to the shape of the user's leg. The strap tab cap is attached to the knee brace with a rivet that extends through a center hole in the strap tab cap. Two posts extend downward from the strap tab cap into slots in the knee brace for limiting the rotation of the strap tab cap and for containing the strap tab in the channels.

11 Claims, 7 Drawing Sheets

STRAP TAB CAP FOR A KNEE BRACE

BACKGROUND OF THE INVENTION

1. Field of the Invention

The present invention relates to knee braces. More particularly, the invention relates to an improved connection device for connecting straps to a knee brace frame.

2. Description of the Related Art

The human knee generally comprises an articulating joint between the thigh and calf muscle groups that supports the weight of the body while a person is standing, walking or running. The joint is primarily held together by four small but strong ligaments, namely, the anterior and posterior cruciate ligaments and the medial and lateral collateral ligaments. The knee is a relatively weak joint and therefore knee injuries arising out of cartilage damage, ligament strain, and other causes are relatively commonplace. Knee injuries are particularly likely to occur during physical activities in which the knees are subjected to significant lateral loads. Among the numerous physical activities in which knee injuries occur, skiing and motorcycle racing have proven to be particularly hazardous.

To help prevent knee injuries, various types of "preventive" knee braces have been proposed to help support and reinforce the knee. FIG. 1 illustrates one particular type of knee brace 10 that is known in the art. The illustrated knee brace 10 is adapted for use on the right leg and includes a rigid frame 11 having an upper member 12 and a lower member 14. Polycentric hinges 16 connect the upper and lower members together along the knee joint. The rigid frame 11 maintains the thigh and calf in the proper alignment and thereby prevents lateral knee joint displacement and hyperextension of the lower leg. A plurality of straps 18 is used to secure the upper member 12 and lower member 14 of the frame 11 to the respective thigh and calf portions of the leg. During fitting, each strap 18 is passed through a loop-shaped connector called a strap tab 20 and is then folded over onto itself for securement with Vecro®. The strap tabs 20 are coupled to the frame 11 by rigid connection devices, called strap tab caps 22, which are attached to the outer surface of the knee brace frame 11.

FIGS. 2 and 3 illustrate a strap tab cap 22 that is known in the art for use with the knee brace of FIG. 1. The cap 22 comprises a substantially disc-shaped main body 23 formed with first and second channels 24, 26 that extend transversely across the bottom side of the cap 22. A portion of a strap tab (shown as 20 in FIG. 1) is captured within one of the channels 24, 26 such that the strap tab 20 is securely coupled to the knee brace frame 11. As best shown in FIG. 3, a pair of screw holes 28, 30 are provided on the bottom side of the cap 22. To secure the cap 22 to the frame 11, a pair of screws 32, 34 are inserted through a pair of holes 36, 38 in the frame 11 and into the screw holes 28, 30.

Although the strap tab cap 22 described in FIGS. 1–3 has proven to be an effective connection device, it has various shortcomings. For example, the strap tab cap 22 must be constructed as a relatively thick member in order to provide sufficiently deep holes 28, 30 for receiving the first and second screws 32, 34. As a result, the strap tab cap 22 has a relatively high profile and therefore projects outwardly from the side of the frame 11. The high profile of the strap tab cap 22 is undesirable because it increases the possibility that the strap tab cap 22 will catch or snag on a foreign object during physical activity.

Another significant shortcoming is related to the manner in which the strap tab cap 22 is mounted to the knee brace frame 11. Because the existing strap tab cap 22 is attached in two locations (i.e., by two screws 32, 34), the strap tab cap is rigidly fixed to the knee brace frame 11. Therefore, the strap tab cap 22 cannot rotate relative to the knee brace frame to allow for adjustment of the strap position. This is a significant problem since the straps on the knee brace must conform to the shape of the user's leg in order to provide maximum comfort and effectiveness.

In an attempt to solve this problem, one manufacturer has proposed a rotatable strap tab mechanism wherein the cap (i.e., connection device) and the strap tab are integrated together as a single plastic member. A fastener extends through a hole in the connection device and the plastic member is able to rotate about the fastener. However, the proposed device is constructed with a high profile and is therefore undesirable for the reasons discussed above. Furthermore, the plastic structure lacks the strength necessary for effective use on a knee brace. Therefore, the proposed device has not gained widespread popularity.

Referring still to FIGS. 1–3, another shortcoming with the illustrated prior art strap tab cap 22 is the potential for the threads in the holes 28, 30 to become worn or stripped over time. When this occurs, the screws 32, 34 are no longer securely engaged within the holes 28, 30 and the strap tab cap 22 may completely detach from the frame 11 and release the strap tab 20.

Yet another shortcoming is the discomfort caused by the screws 32, 34 that are used to attach the strap tab cap 22 to the knee brace frame 11. Because the screws are inserted from the inside of the frame, the screw heads can press against the user's leg. As a result, a relatively thick padded insert is required along the inside of the frame 11 to help minimize the discomfort. However, the padded insert does not entirely alleviate the problem and adds undesirable expense.

Yet another shortcoming is the large number of screws required for attaching the strap tab caps to the knee brace frame. A knee brace having four caps requires eight screws that can be cumbersome and time consuming to insert during assembly. Furthermore, each of the screws can back out of the holes 28, 30 in the cap 22 over time, thereby requiring maintenance by the user.

Thus, there remains a very real and substantial need for an improved strap tab cap for attaching strap tabs to knee brace frame. It is desirable that such a strap tab cap has a low profile to avoid catching or snagging on other objects during physical activity. It is also desirable that such a strap tab cap is rotatably mounted on the knee brace frame to allow for improved fitting of the straps. It is also desirable that such a strap tab cap is constructed of a durable material that is resistant to corrosion. Finally, to be practical, it is desirable that such a strap tab cap is inexpensive to manufacture and is aesthetically appealing. The present invention addresses this need.

SUMMARY OF THE INVENTION

The preferred embodiments of the present invention provide a new and improved strap tab cap adapted for securely connecting strap tabs to the rigid frame of a knee brace. The preferred embodiments of the cap are constructed with a low profile that substantially reduces the possibility that the cap will catch or snag on a foreign object. The preferred embodiments of the cap are also rotatably mounted to the knee brace frame such that the straps can be adjusted to better conform to the shape of the user's leg.

In accordance with one aspect of the present invention, a cap is presented generally comprising: a main body formed with a central hole, at least one post projecting downward from the bottom side of the main body, and at least one channel formed along the bottom side of the main body. The cap has a rounded top surface wherein the main body has a relatively thick middle portion which tapers toward thin edges. The channel extends transversely across the cap for receiving a strap tab. The post is inserted into a slot in the knee brace frame to limit the rotation of the strap tab cap.

The preferred embodiments of the present invention have tremendous structural integrity and therefore can withstand the application of large forces over long periods of time. The preferred embodiments of the cap are also easy to assemble, inexpensive to manufacture and do not use screws that can cause discomfort to the user along the inner surface of the knee brace frame.

The strap tab cap is described herein with particular reference to use with a knee brace; however, it will be understood that the strap tab cap is equally suitable for numerous other applications.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENT

FIGS. 4–7 illustrate a preferred embodiment of a strap tab cap 40 for securely attaching one or two strap tabs to a knee brace frame in accordance with the present invention. The cap 40 preferably includes, generally, a main body 42, first and second channels 46, 48 extending transversely across the bottom side of the main body, and first and second posts 50, 52 extending downward from the main body.

Figure 1:
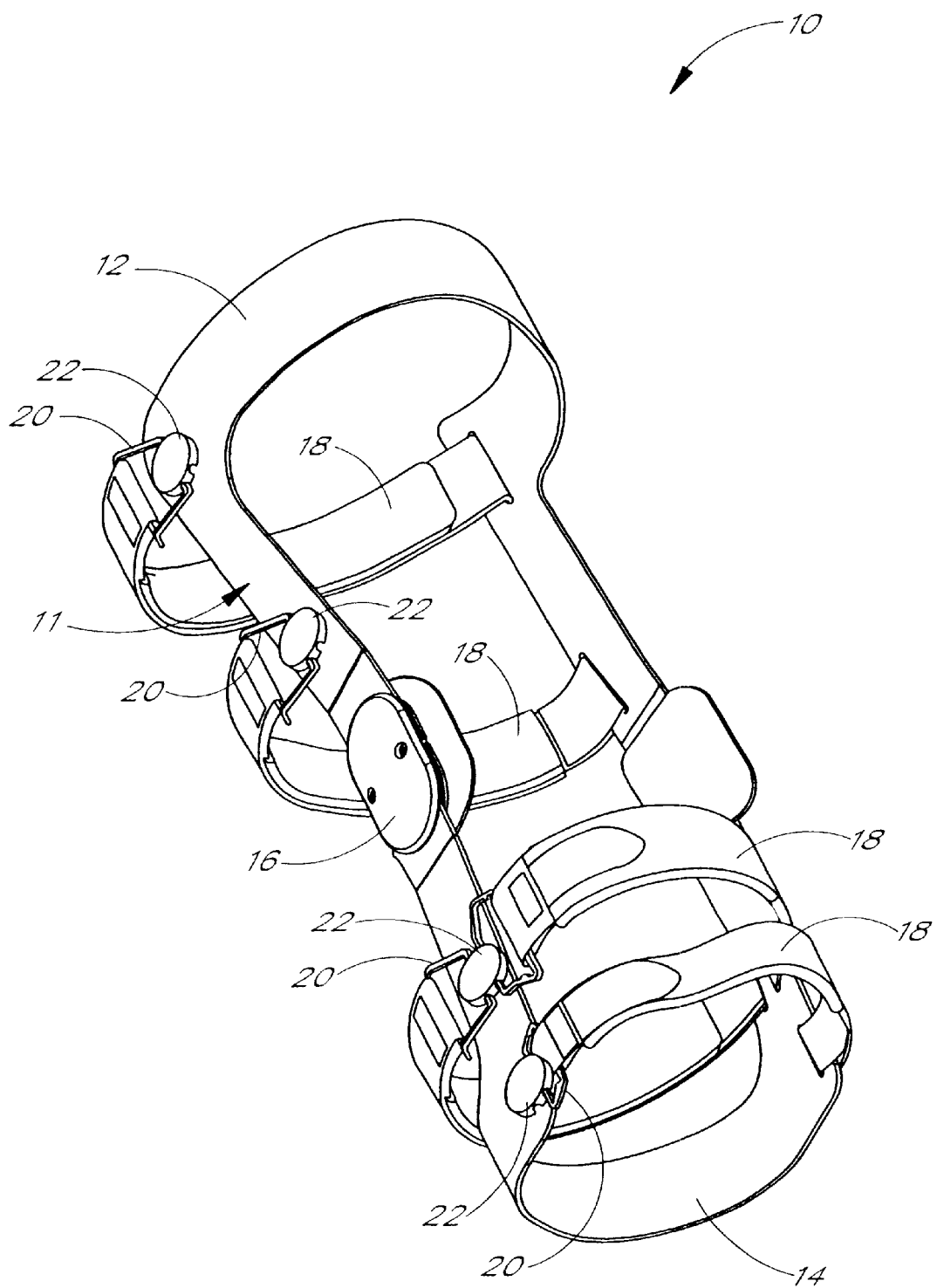
FIG. 1 is a perspective view of a knee brace of the type known in the art.
Figure 2:
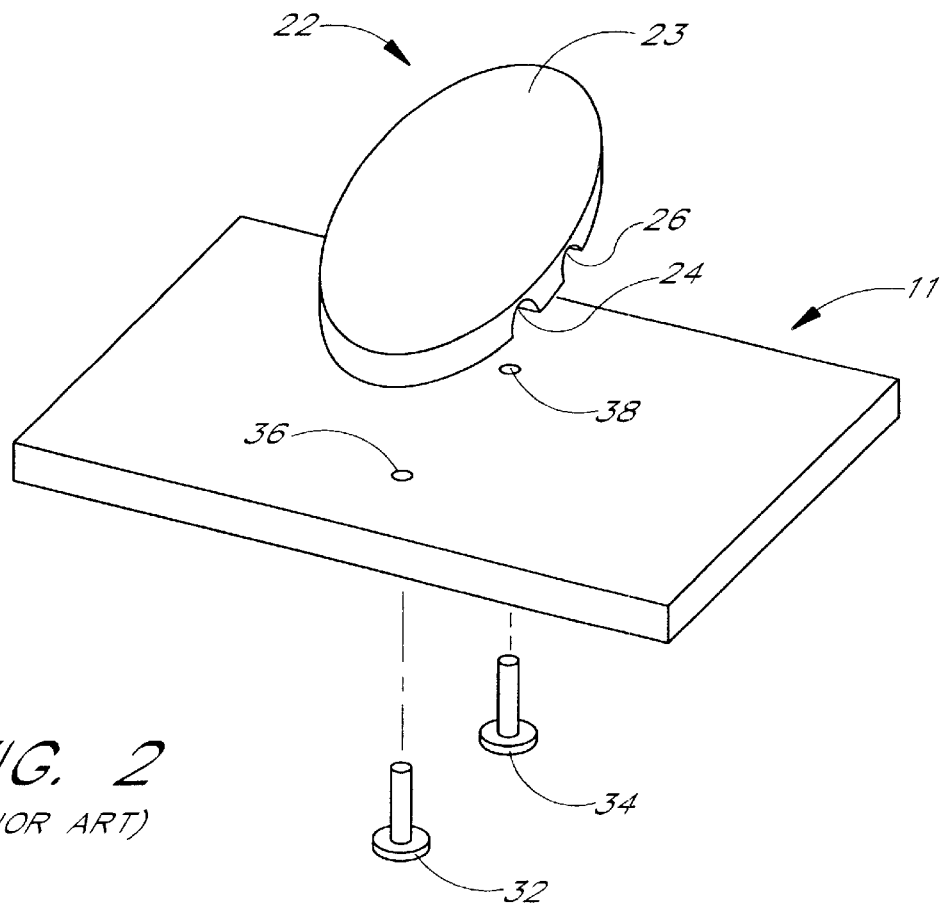
FIG. 2 is an exploded view illustrating how a prior art strap tab cap is attached to the knee brace of FIG. 1.
Figure 3:
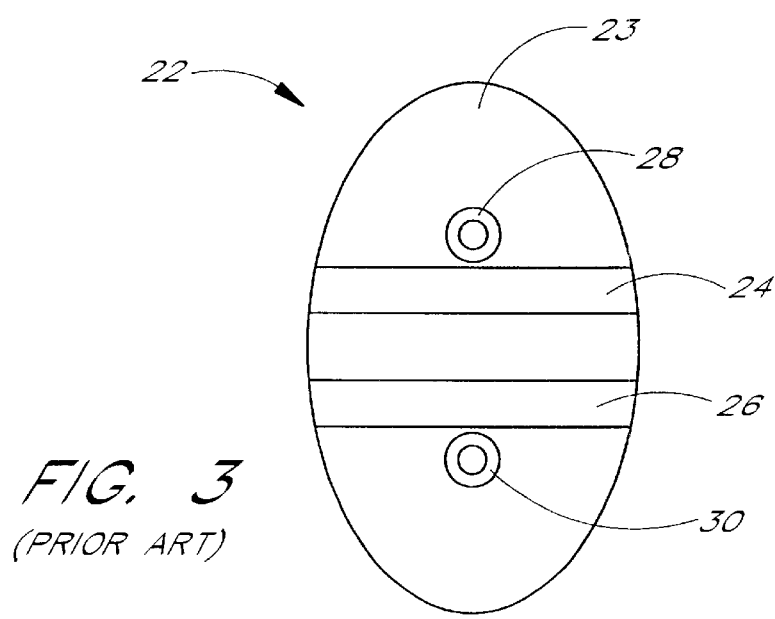
FIG. 3 is a bottom view of the strap tab cap of FIG. 2.
Figures 4, 5:
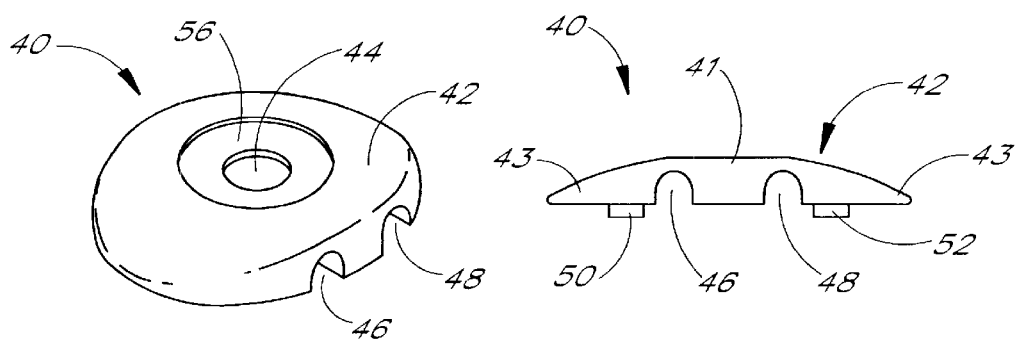
FIG. 4 is a perspective view of a preferred embodiment of a strap tab cap according to the present invention.
FIG. 5 is a side view of the strap tab cap of FIG. 4.

As best illustrated in FIG. 5, the main body 42 has a substantially flat shape and is preferably formed with a rounded top surface. Accordingly, the main body 42 has a relatively thick middle portion 41 that tapers toward the edges to provide relatively thin end portions 43. The rounded top surface advantageously provides a low profile shape that substantially reduces the likelihood that the cap will catch or snag on a foreign object during physical activity.

Figures 6, 7:
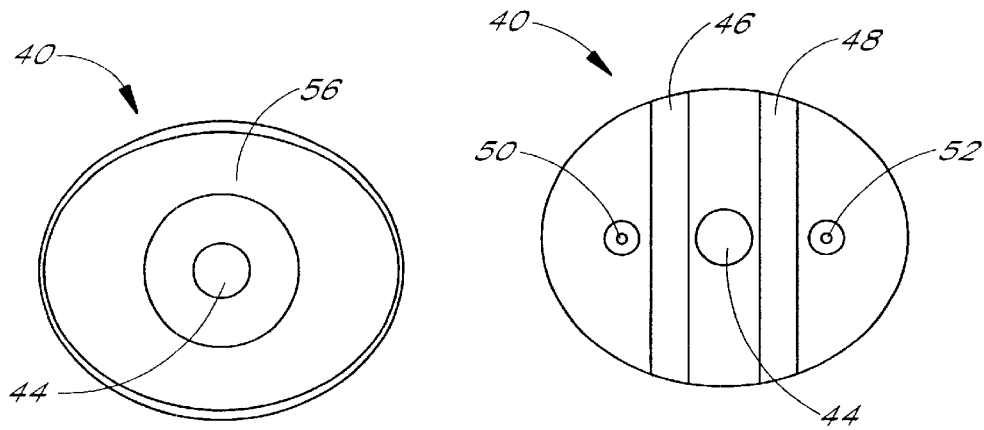
FIG. 6 is a top view of the strap tab cap of FIG. 4.
FIG. 7 is a bottom view of the strap tab cap of FIG. 4.

Referring now to FIGS. 5 and 6, the main body 42 is preferably elliptical in shape having a length along the long axis of about 1.125" and a length along the short axis of about 1.00". The hole 44 located at the center of the main body 42 is provided for receiving a rivet for attachment to the knee brace frame. Preferably, the rivet used with the present invention has a large diameter head that extends laterally over the first and second channels 46, 48 to prevent deformation of the cap and increase the strength of the assembly. Because the rivet passes through the middle portion 41 wherein the cap 40 is thickest, the cap has tremendous structural integrity and provides an extremely durable and rugged connection device. The middle portion 41 preferably has a maximum thickness of about 0.150" to 0.200", and most preferably has a maximum thickness of 0.175". Of course, it will be appreciated that the dimensions of the strap tab cap can have any size and the ranges provided herein are merely exemplary for use according to the application with a knee brace.

FIG. 7 illustrates the configuration of the bottom side of the cap 40. The cap 40 is formed with two spaced, generally parallel channels 46, 48 that preferably extend transversely across the short axis of the elliptical main body 42. However, in an alternative embodiment, the channels may be formed to extend across the long axis of the elliptical main body. The channels 46, 48 are located in the thick middle portion on opposite sides of the central hole 44. Each of the channels 46, 48 is sized to receive a portion of a strap tab. Strap tabs may be attached to one or both sides of the cap, depending on the location of the cap on the knee brace frame. Because the strap tabs and the cap are constructed as separate pieces, the strap tabs can be moved independently of the cap. Therefore, the strap tabs can be rotated (or flipped) up and down relative to the cap while contained in the channels to facilitate the insertion of the strap through the strap tab.

At least one post is provided on the bottom side of the cap 40. In the illustrated embodiment, two posts 50, 52 are provided which are located just outside of the channels 46, 48. However, in alternative embodiments, the posts may be located in any position along the bottom side of the cap. Each of the posts 50, 52 is preferably cylindrical in shape with a diameter of about 0.15". The posts 50, 52 preferably extend about 0.10" downward from the bottom of the cap. It should be noted that all the caps on a knee brace may be formed of substantially the same construction for the sake of uniformity and ease of manufacturing.

Figures 8, 9:
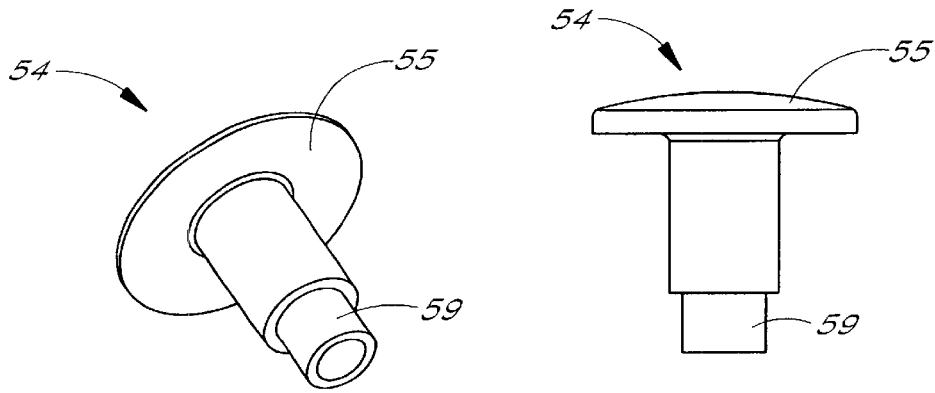
FIG. 8 is a perspective view of a rivet used to attach the strap tab cap of FIG. 4 to a knee brace frame.
FIG. 9 is a side view of the rivet of FIG. 8.

FIGS. 8 and 9 illustrate a rivet 54 that may be used to attach a strap tab cap to the knee brace frame. Although a rivet is the preferred fastener, any suitable fastener may be used with the present invention. Referring now to FIGS. 4–9, the rivet 54 has a head 55 that fits into a recess 56 formed in the top surface of the main body 42 of the cap 40.

This feature helps maintain the low profile character of the cap 40 while providing an aesthetically pleasing appearance. The distal tip 59 of the rivet 54 is constructed to expand in the radial direction upon application of sufficient force. The rivet 54 used in the present invention has numerous advantages over the screws used in the prior art. For example, rivets are quicker and easier to apply and therefore save time and expense during assembly. In addition, rivets do not utilize threads that can strip or break over time. Furthermore, a rivet is very resistant to loosening and therefore does not require any maintenance.

Figure 10:
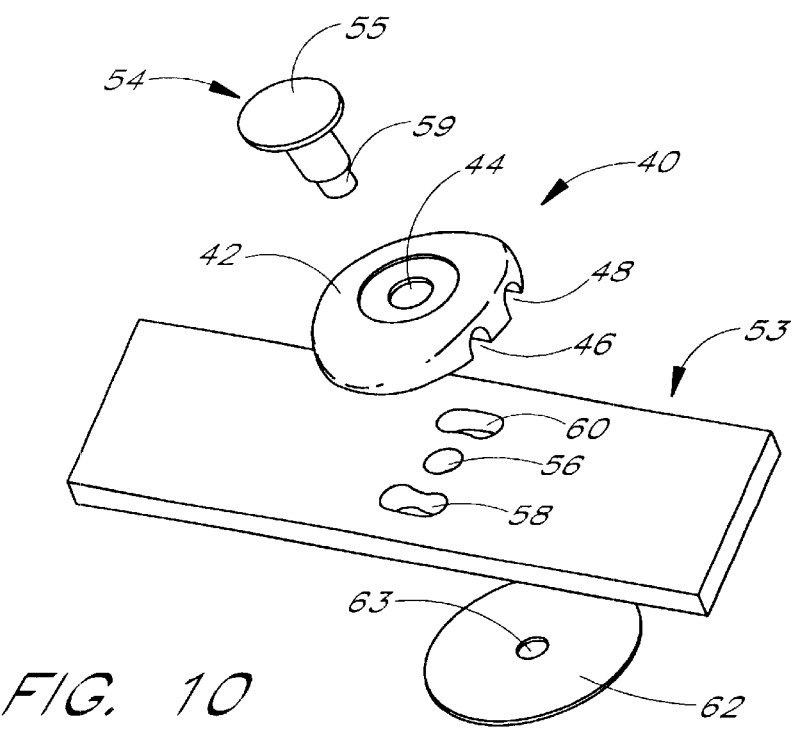
FIG. 10 is an exploded view showing how the strap tab cap of FIG. 5 is attached to the knee brace frame.

FIG. 10 is an exploded view illustrating one preferred method for mounting the cap 40 to the knee brace frame 53. The rivet 54 is inserted through the central hole 44 in the main body 42, through a hole 56 in the frame 53 and through a hole 63 in a washer 62. The distal tip 59 of the rivet 54 is deformed to a size larger than the hole 63 in the washer 62 to secure the cap 40 to the knee brace frame 53. The washer 62 is provided to spread the load from the rivet 54 across a substantial area along the inside of the knee brace frame 53. A pair of slots 58, 60 are formed in the frame 53 through which the posts 50, 52 are inserted.

In a significant feature of the present invention, a strap tab cap according to the present invention has the ability to rotate relative to the knee brace frame to improve the comfort and effectiveness of the knee brace straps. With reference to FIGS. 5 and 10, the posts 50, 52 on the bottom of the cap 40 move within the slots 58, 60 as the cap rotates. The range of rotation of the cap 40 is determined by the length of the slots 58, 60. In one preferred embodiment, the slots 58, 60 are sized to provide the cap 40 with a range of angular rotation of approximately +/−15 degrees from normal. The slots 58, 60 are preferably curved in shape to track the path of the posts 50, 52 as the cap 40 rotates about the rivet 54. Although the illustrated embodiment is shown with slots that extend all the way through the frame, the slots may also be formed as recesses in the frame.

Figure 11:
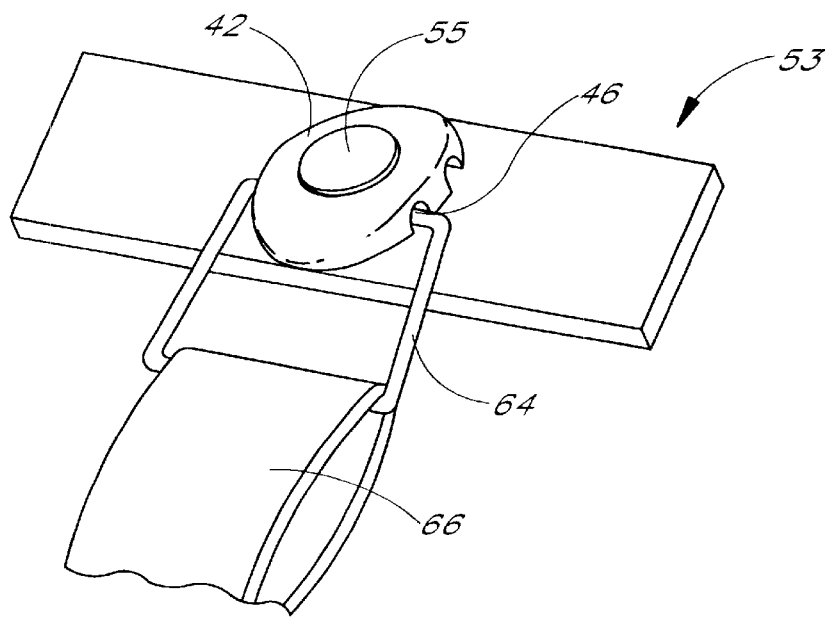
FIG. 11 is a perspective view showing the strap tab cap of FIG. 5 attached to the knee brace with a strap tab extending through a channel in the cap.

FIG. 11 illustrates the strap tab cap 40 with a strap tab 64 extending through the first channel 46. The strap tab 64 is a loop-shaped member that provides a means for coupling the strap 66 to the knee brace frame 53. The strap 66 is inserted through the strap tab 64 and is then folded over onto itself. Velcro®, snaps, buckles or any other suitable material may be used for securing the strap 66.

As discussed above, in one embodiment of the present invention, the head 55 of the rivet 54 extends broadly over the top surface of the strap tab cap 40. This feature prevents the strap tab cap 40 from deforming and thereby ensures that the middle portion of the strap tab cap is in contact with the surface of the knee brace frame at all times. As a result, the strap tab 64 is prevented from slipping out of the channel 46 through a clearance between the strap tab cap and the knee brace frame. Furthermore, the posts (shown as 50 and 52 in FIG. 5) provide an additional barrier that ensures that the strap tab 64 cannot slide out of the channel 46 from underneath the cap 40.

Once mounted, the cap 40 cannot become disconnected from the knee brace frame 53 without removing the rivet or breaking the cap. As a result, the present invention provides a very sturdy and rugged connection mechanism for attaching a strap tab to a knee brace frame. The tremendous structural integrity of the strap tab cap 40 is very important because the strap tab cap 40 is repeatedly subjected to large loads during use in physical activity.

Figure 13:
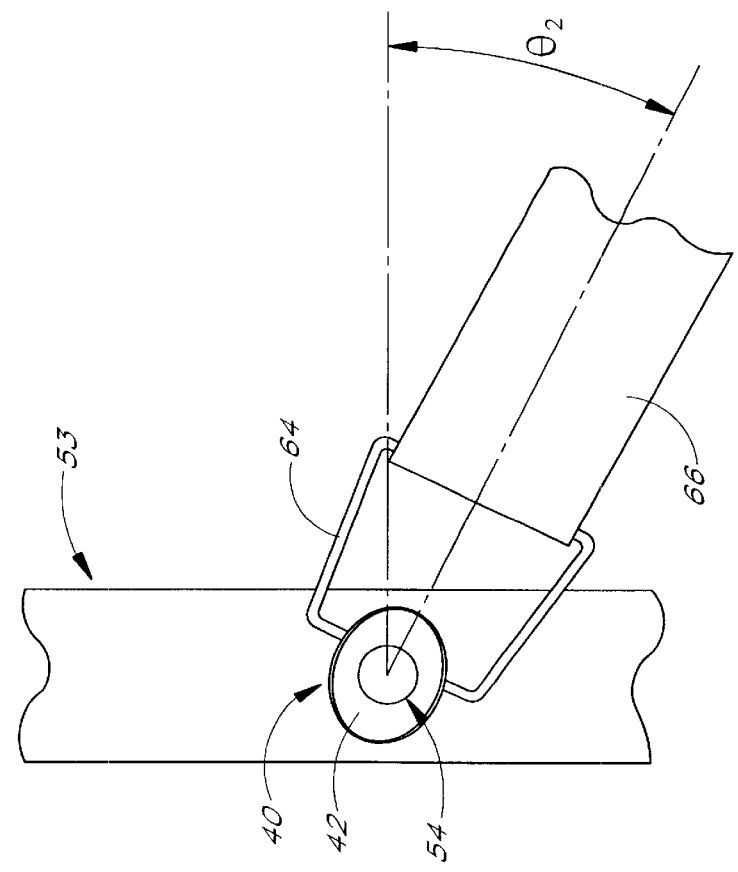
FIGS. 12 and 13 illustrate the rotational capability of the strap tab cap of FIG. 5.
Figure 12:
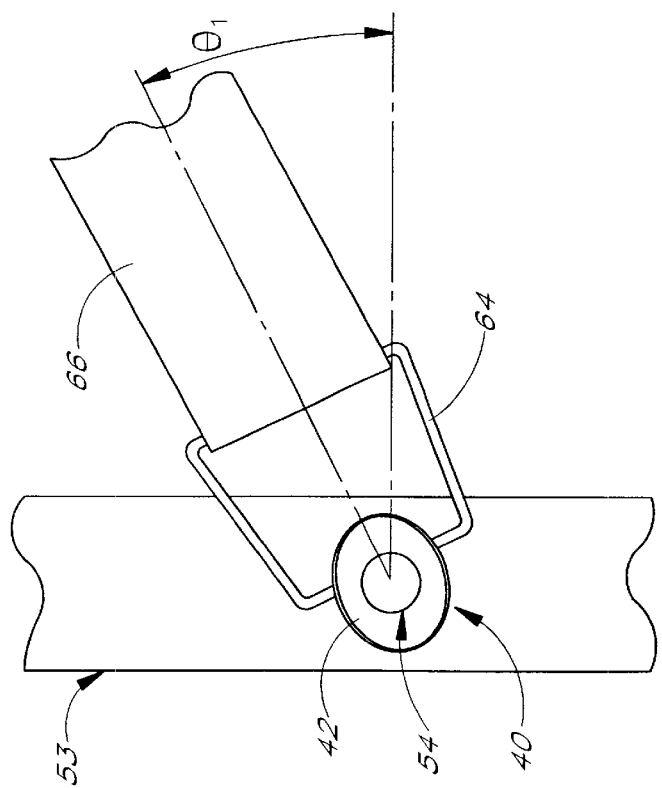

FIGS. 12 and 13 illustrate the ability of the cap 40 to rotate upward relative to the knee brace frame 53 at an angle $\theta_1$ and downward at an angle $\theta_2$. The maximum angles of rotation are determined by the size of the slots in the knee brace frame. As discussed above, the ability of the strap tab cap to rotate relative to the knee brace allows the angle of the strap 66 attachment to be adjusted according to the shape of the user's leg. This feature improves the comfort and effectiveness of the knee brace without sacrificing stability or support of the knee joint. The rotation of the cap 40 also improves the comfort of the knee brace by allowing the strap 66 to move with the changes in the shape of the user's leg that naturally occur during physical activity.

The preferred embodiments of the strap tab cap are molded from a durable plastic, such as nylon. The strap tab is preferably formed of 4130 steel. The rivet may be formed of stainless steel, or any other suitable material.

Figure 14:
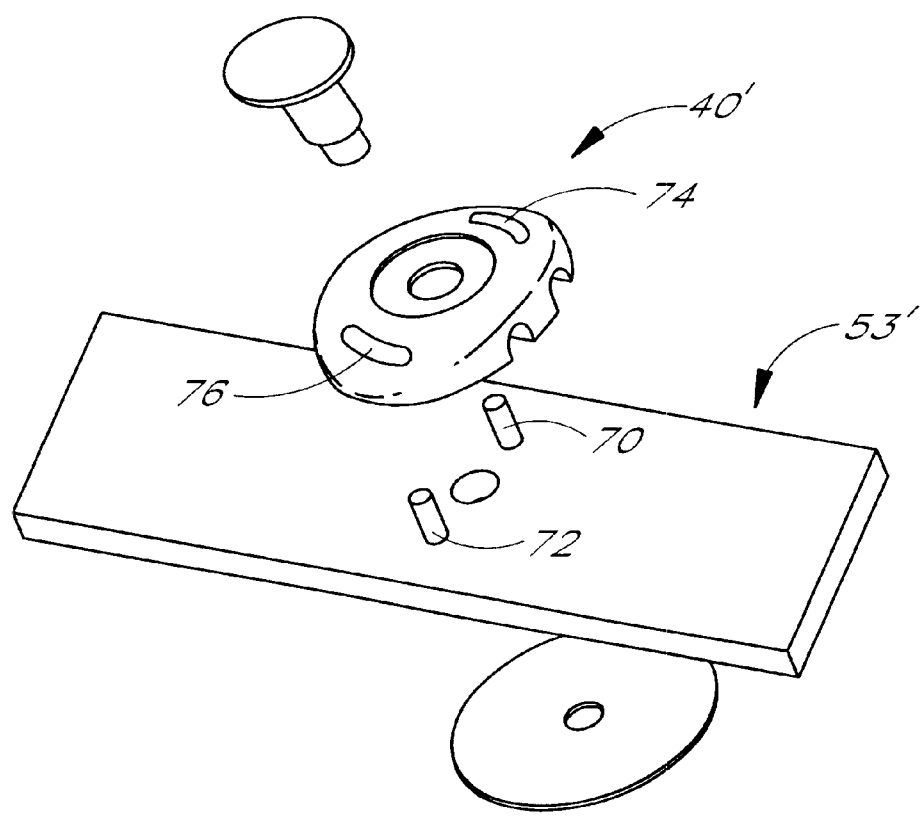
FIG. 14 is an exploded view showing an alternative embodiment of a strap tab cap of the present invention wherein the posts are located on the knee brace frame and the slots are formed in the cap.
Figures 15A, 15B:
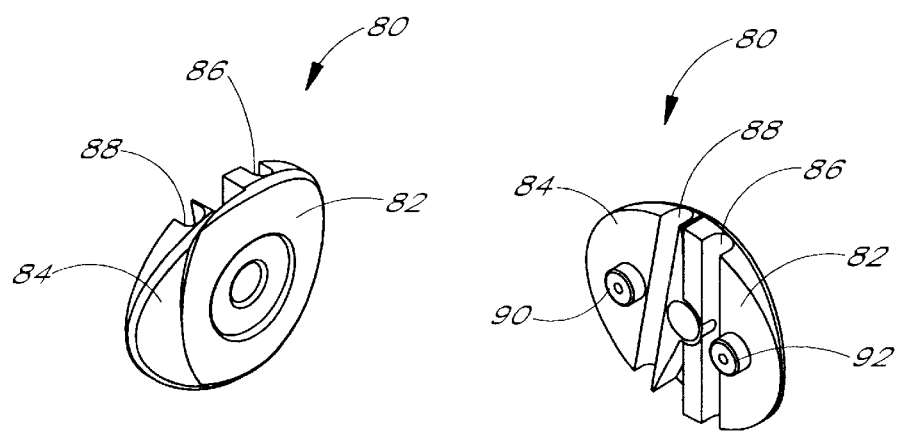
FIGS. 15A and 15B are perspective views of another embodiment of a strap tab cap according to the present invention wherein the strap tab cap comprises two separate halves that can rotate independently of each other.

In various other embodiments of the present invention, alternative structures may be provided for limiting the rotation of the strap tab cap. FIG. 14 illustrates another preferred embodiment of a strap tab cap 40' wherein posts 70, 72 are located on the exterior of the knee brace frame 53' and slots 74, 76 are provided in the strap tab cap 40'.

FIGS. 15A–17 illustrate yet another preferred embodiment of a strap tab cap 80 according to the present invention. In this embodiment, the strap tab cap 80 comprises two separate halves 82, 84 that are coupled to the knee brace frame by a common fastener, yet can rotate independently of each other. The first half 82 includes a first channel 86 and a first post 92. The second half 84 includes a second channel 88 and a second post 90. As in the previously described embodiments, the posts 90, 92 extend into slots in the knee brace frame for limiting the range of rotation and for providing a barrier to prevent the strap tabs from escaping from the channels 86, 88. This embodiment of the present invention is particularly advantageous for use with two strap tabs. Due to the ability of the separate halves 82, 84 to rotate independently of each other, the two strap tabs (and therefore the two straps) can also be adjusted independently of each other for maximum comfort and effectiveness.

Figures 16A, 16B:
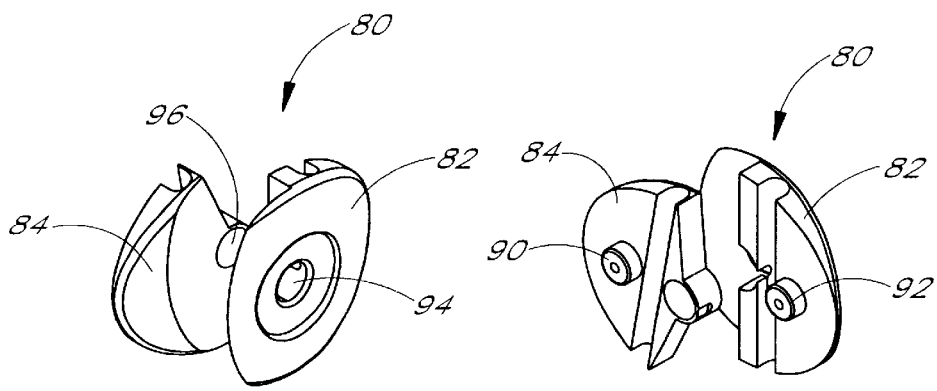
FIGS. 16A and 16B are exploded views of the strap tab cap of FIG. 15A.
Figure 17:
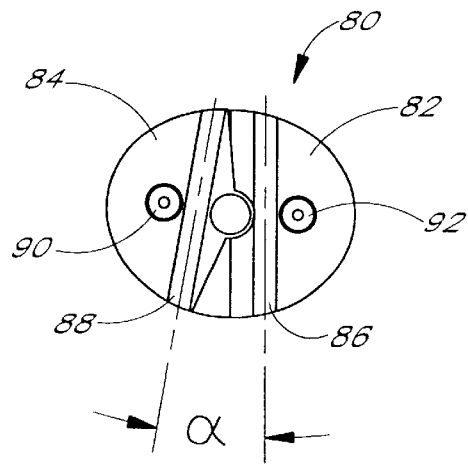
FIG. 17 is a bottom view of the strap tab cap of FIG. 15A.

As best illustrated in FIGS. 16A and 16B, the two halves 82, 84 are formed with central holes 94, 96 through which a rivet extends to couple the halves to the knee brace frame and also to each other. FIG. 17 is a bottom view of the strap tab cap 80 illustrating how the two halves may rotate independently of each other within a limited range such that the centerlines of the channels 86, 88 form an angle α. The maximum angle can be varied according to the desired use; however, in one preferred embodiment, the maximum angle formed by the centerlines of the channels 86, 88 is about 20 degrees.

From the foregoing, it will be appreciated that each of the preferred embodiments of the strap tab cap can be attached to a knee brace frame quickly and easily and has excellent structural integrity. In addition, the each of the preferred embodiments of the strap tab cap is very versatile and can be used in a broad range of other applications wherein a strap is used, such as on luggage or backpacks.

The above presents a description of the best mode contemplated for a strap tab cap according to the present invention, and of the manner and process of making and using it, in such full, clear, concise, and exact terms as to enable any person skilled in the art to which it pertains to make and use this invention. The embodiments of the strap tab cap described herein are, however, susceptible to modifications and alternate constructions which are fully equivalent. Consequently, it is not the intention to limit this strap tab cap to the particular embodiments disclosed. On the contrary, the intention is to cover all modifications and alternate constructions coming within the spirit and scope of the invention as generally expressed by the following claims, which particularly point out and distinctly claim the subject matter of the present invention.

What is claimed is:

1. A cap for attaching a strap tab to a knee brace frame, comprising:
    a substantially flat main body having top and bottom sides and formed with a central hole for receiving a fastener, said main body being capable of rotation about said fastener;
    a post projecting from said bottom side of said main body, said post formed to extend into a slot in said knee brace frame to limit said rotation of said main body; and
    a channel formed along said bottom side of said main body, said channel adapted to receive said strap tab for securely attaching said strap tab to said knee brace frame.

2. The cap of claim 1, wherein said fastener is a rivet having a head and a distal end.

3. The cap of claim 2, further comprising a recess formed in said top side of said main body around said hole for receiving said head of said rivet.

4. The cap of claim 2, further comprising a washer located along said knee brace frame on a side opposite to said cap for receiving said distal end of said rivet.

5. The cap of claim 1, wherein said main body is elliptical in shape with a long axis and a short axis, said main body formed with a thick middle portion that tapers along said long axis toward first and second thin edges to provide a low profile.

6. The cap of claim 5, wherein said channel extends perpendicular to said long axis of said cap.

7. A cap for attaching first and second strap tabs to a knee brace frame, comprising:
    a substantially flat main body having top and bottom sides and formed with a central hole;
    a rivet extending through said central hole for securely attaching said main body to said knee brace, said rivet having a head and a distal end, said main body being capable of rotation about said rivet, said main body formed with a recess around said hole for receiving said head of said rivet;
    first and second posts projecting downward from said bottom side of said main body, said first and second posts formed to extend into first and second slots formed in said knee brace frame to limit said rotation of said main body relative to said knee brace frame; and
    first and second channels extending along said bottom side of said main body perpendicular to a long axis, said first and second channels adapted to receive a portion of said first and second strap tabs for securely attaching said first and second strap tabs to said knee brace frame.

8. The cap of claim 7, wherein said main body further comprises a first half including said first channel and said first post and a second half including said second channel and said second post wherein said first half and said second half can each rotate independently about said rivet.

9. An assembly for attaching a strap tab to a surface, comprising:
    a substantially flat main body having top and bottom sides and formed with a central hole for receiving a fastener, said main body being capable of rotation about said fastener;
    a post projecting from said bottom side of said main body, said post formed to extend into a slot in said surface to limit said rotation of said main body about said surface; and
    a channel formed along said bottom side of said main body, said channel adapted to receive said strap tab for securely attaching said strap tab to said surface.

10. A cap for attaching a strap tab to a knee brace frame, comprising:
    a substantially flat main body having a bottom side and formed with a central hole for receiving a fastener, said main body being capable of rotation about said fastener, said main body also being formed with a slot;
    a post projecting upward from said knee brace frame, said post formed to extend into said slot in said main body to limit said rotation of said main body about said fastener; and
    a channel formed along said bottom side of said main body, said channel adapted to receive said strap tab for securely attaching said strap tab to said knee brace frame.

11. A method of attaching a strap tab to a knee brace frame, comprising:
    providing a substantially flat main body having top and bottom sides and formed with a central hole for receiving a fastener, said main body having a channel formed along said bottom side for receiving a portion of said strap tab;
    placing said main body against a surface of said knee brace frame with a portion of said strap tab in said channel; and
    inserting a fastener through said central hole and through a hole in said knee brace frame to rotatably couple said main body to said knee brace frame.

* * * * *